United States Patent
Van Der Mark et al.

(10) Patent No.: US 6,327,488 B1
(45) Date of Patent: Dec. 4, 2001

(54) DEVICE FOR LOCALIZING AN OBJECT IN A TURBID MEDIUM

(75) Inventors: Martinus B. Van Der Mark; Nicolaas A. A. J. Van Asten; Wilhelmus M. Walraven, all of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/073,508

(22) Filed: May 6, 1998

(30) Foreign Application Priority Data

May 9, 1997 (EP) .................................................. 97201404

(51) Int. Cl.⁷ ...................................................... A61B 5/00
(52) U.S. Cl. .......................... 600/407; 600/473; 600/476; 356/432; 385/16
(58) Field of Search ..................................... 600/407, 473, 600/475–478; 385/15, 16, 31, 53; 356/432–435, 445, 448, 244

(56) References Cited

U.S. PATENT DOCUMENTS 5,876,339 * 3/1999 Lemire ................................. 600/476
5,907,406 * 5/1999 Papaioannou et al. ............... 600/476
5,987,351 * 11/1999 Chance .................................. 600/476

FOREIGN PATENT DOCUMENTS

| 0178366A2 | 4/1986 | (EP) | G02B/6/16 |
| WO 9620638 | 7/1996 | (EP) | A61B/5/00 |
| WO9710568 | 3/1997 | (WO) | G06T/5/20 |

* cited by examiner

Primary Examiner—Ruth S. Smith
(74) Attorney, Agent, or Firm—John F. Vodopia

(57) ABSTRACT

The light to be generated by a light source in a device for localizing an object in a turbid medium is successively coupled into the turbid medium from different directions by use of an optical detection unit. The light coupled in is transported in different directions through the turbid medium. A part of the light emanating from the turbid medium is measured by use of photodetectors. An image of the interior of the turbid medium is reconstructed by optical tomography on the basis of the measured intensities. The device includes structure which reduces variations in the intensity of the light coupled into the turbid medium from the same direction in order to reduce errors occurring on repeated executions of the measurements for successively localizing the object.

8 Claims, 3 Drawing Sheets

DEVICE FOR LOCALIZING AN OBJECT IN A TURBID MEDIUM

FIELD OF THE INVENTION

The invention relates to a device for localizing an object in a turbid medium, which device includes a light source and a holder for accommodating the turbid medium, which holder is provided with a plurality of entrance openings for coupling the light to be generated by the light source into the turbid medium and a plurality of exit openings, whereto photodetectors are coupled, which device also includes a selection unit for optically coupling the light source to an entrance opening to be selected from the plurality of entrance openings.

BACKGROUND OF THE INVENTION

A device of this kind is known from the international patent application WO 96/20638. In the context of the cited patent application a light source is to be understood as a source which emits electromagnetic radiation of a wavelength in a range of between 400 and 1400 nm. The known device can be used for the imaging of the interior of biological tissues. In medical diagnostics the device could be used for the imaging of tumors in breast tissue. Light generated by the light source in the known device is applied to the turbid medium via successively selected entrance openings in the holder, the same entrance opening being selected several times. Subsequently, detectors at the exit openings of the holder measure the intensity of the light having been transported through the turbid medium along different optical paths from the selected entrance opening. The measured intensities are used to localize the object in the turbid medium. It is a drawback of the known device that in the localizing of the object in the turbid medium on the basis of the measured intensities an error occurs relative to the actual position of the object in the turbid medium.

SUMMARY OF THE INVENTION

It is inter alia an object of the invention to provide a device in which the error in localizing the object in the turbid medium is mitigated. To achieve this, the device according to the invention is characterized in that it includes means for counteracting variations in a transmission of an optical path between the light source and the selected entrance opening. The invention is based on the idea that errors arise in the localization of the object in the turbid medium because variations occur in the intensity of the light through the selected entrance opening when this entrance opening is selected several times during the execution of successive measurements on the object. The use of means which counteract the variations in the light intensity through the selected entrance opening results in a smaller contribution to the error in the localization of the object in the turbid medium.

A special device according to the invention is characterized in that the selection unit is provided with an entrance light conductor and exit light conductors, a first end of said entrance light conductor being optically coupled to the light source whereas a second end is positioned so as to be displaceable for the optical coupling to a first end of one of the exit light conductors, a second end of said exit light conductor being coupled to the selected entrance opening and a numerical aperture of the first end of each exit light conductor being larger than a numerical aperture of the second end of the entrance light conductor. Because of the larger numerical aperture of the first end of the exit light conductor relative to the second end of the entrance light conductor, the transmission is rendered less dependent on a positioning error of the second end of the entrance light conductor relative to the first end of the exit light conductor. This results in a smaller variation of the transmission of the optical path between the light source and the selected entrance opening in the case of repeated selection of the same light source.

A further device according to the invention is characterized in that the entrance light conductor of the selection unit includes an optical fiber of a first type and that each exit light conductor of the selection unit includes an optical fiber of a second type. The use of optical fibers enables a compact construction of the device.

A further device according to the invention is characterized in that each exit light conductor also includes an optical fiber of a third type which has a property deviating from that of the optical fiber of the second type and is optically coupled, via a fiber-optical connector unit, to the optical fiber of the second type of the same exit light conductor. As a result of the use of an optical fiber of the third type, having optical or mechanical properties which deviate from those of the optical fibers of the second type, the optical fibers of the second type as well as those of the third type can be optimized for a specific application in the device.

A further device according to the invention is characterized in that the optical fiber of the second type contains quartz. As a result of this choice, the transmission of the optical fiber of the second type can be optimized because of the low damping factor of the optical fiber of the second type.

A further device according to the invention is characterized in that the optical fiber of the third type contains a synthetic material. Because of a low elasticity modulus of an optical fiber of the third type, this choice simplifies the coupling of the device to and the assembly with the holder in a small space.

A further device according to the invention is characterized in that the fiber-optical connector unit includes a first section which contains a second end of the optical fiber of the second type and a second section which contains a first end of the optical fiber of the third type, a light-absorbing material being arranged between the first section and the second section and being provided with a light-conducting channel for optically coupling the optical fiber of the second type to the optical fiber of the third type. Because the light-absorbing material in the connector unit is provided with several channels, crosstalk between adjacently situated transmission paths in the optical connector unit is counteracted. The crosstalk occurring may be due, for example to the non-coaxial positioning of the second end of an optical fiber of the second type relative to the first end of the optical fiber of the third type, so that reflection causes a part of the light to be conducted to a first end of a neighboring optical fiber of the third type.

A further device according to the invention is characterized in that the light-absorbing material also has elastic properties. This step offers a greater tolerance in respect of the dimensional accuracy of the areas of the first and the second section adjoining one another in the assembled state of the optical connector unit. Because of the greater tolerance, the manufacture of the first and second sections of the optical connector unit can be simpler and less expensive.

BRIEF DESCRIPTION OF THE DRAWINGS

The above and other, more detailed aspects of the invention will be described in detail hereinafter, by way of example, with reference to the drawings. In the drawings.

DETAILED DESCRIPTION OF A PREFERRED EMBODIMENT

Figure 1:
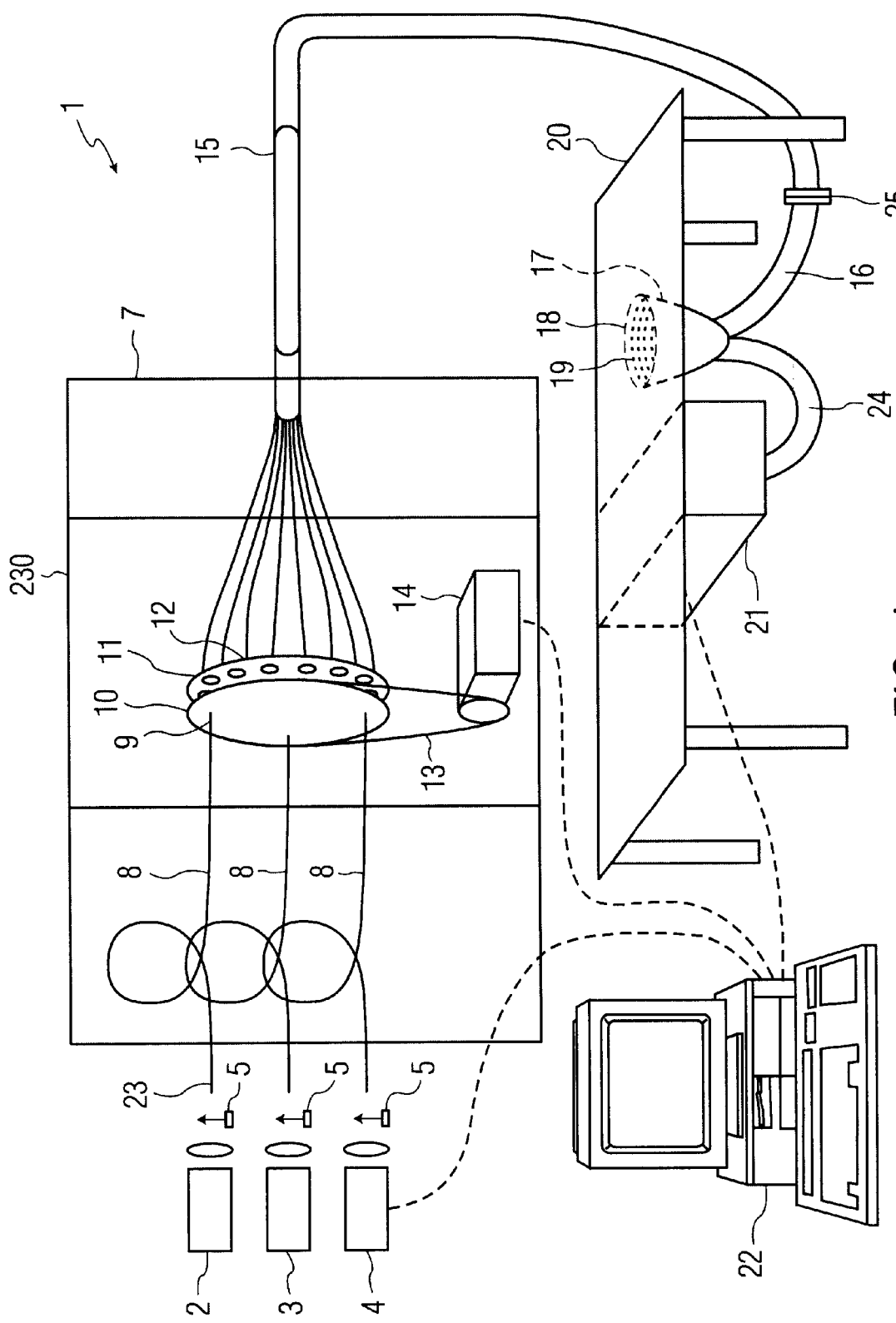
FIG. 1 shows a device for performing measurements on a turbid medium.

FIG. 1 shows a device for performing measurements on a turbid medium. The device 1 includes a light source 2, a holder 17 for accommodating a turbid medium, said holder being provided with a plurality of, for example 256 entrance openings 18 and a plurality of, for example 256 exit openings 19 whereto a photodetector unit 21 is coupled. The device 1 also includes a table 20 for accommodating a human body, said table being provided with the holder 17 for receiving a turbid medium. The device also includes a selection unit 7 for optically coupling the light source 2 to an entrance opening 18 to be selected from the plurality of entrance openings, and a control unit 22. A device of this kind can be used for performing medical diagnostic examinations by means of optical tomography. To this end, the body is positioned on the table 20 in such a manner that the holder 17 contains the part of the body to be examined, for example a part of a breast.

A laser diode, for example of the Philips type CQL-822, is an example of a light source which is suitable for use in the device. The wavelength of this type of laser is 660 nm and its output power amounts to 100 mW. In order to have a light source available which is capable of generating light of different wavelengths during the measurements, for example, three laser diodes 2, 3, 4 are used, each of which generates light in a different wavelength range; one of the three laser diodes 2, 3, 4 is then optically coupled to the selected entrance opening 18 of the holder 17 by means of the selection unit 7 and optical shutters 5 in the optical paths between the laser diodes 2, 3, 4 and the selection unit 7 interrupt the optical coupling between the non-selected laser diode and the selection unit. The selection unit also includes entrance light conductors 8, a positioning unit 23 and exit light conductors 15. The three entrance light conductors 8 couple the laser diodes 2, 3, 4 to the selection unit. The entrance light conductors comprise, for example optical fibers of a first type, the first ends 23 of the optical fibers 8 of the first type being optically coupled to the laser diodes 2, 3, 4, via the optical shutters 5. The entrance light conductors may also include a geometrical-optical system. The exit light conductors 15 optically couple the selection unit 7 to the entrance openings 18 of the holder 17. The exit light conductors comprise, for example optical fibers of a second type, but may also be constructed as a geometrical-optical system.

The positioning unit 23 includes a first carrier 10 and a second carrier 11. The carriers 10, 11 preferably have a circular shape and can be positioned coaxially relative to one another. The two ends 9 of the optical fibers 8 of the first type are provided in the form of a first circle on the first carrier 10 and the first ends 12 of the optical fibers 15 of the second type are provided in the form of a second circle on the second carrier 11, the radius of the first circle being equal to the radius of the second circle. In order to position the first carrier 10 relative to the second carrier 11, the positioning unit 23 is provided with a step motor 14 and a transmission 13 to the first carrier 10. The transmission may be constructed, for example as a toothed belt transmission. The selection of an entrance opening 18 of the holder 17 is performed by means of the control unit 22 which generates motor control signals for the step motor 14 for this purpose in such a manner that the end 9 of one of the optical fibers 8 of the first type, being optically coupled to the selected laser diode 2, is arranged so as to be coaxial with the end 12 of one of the optical fibers 15 of the second type which is optically coupled to the entrance opening 18 to be selected in the holder 17.

In order to achieve a short switching time, the radius of the circular carriers 10, 11 can be minimized so that the mass inertia of the carriers is reduced. If necessary, a third circle can be provided on the second carrier 11, a part of the first ends of the optical fibers 15 then being connected to said third circle; in that case an additional mechanical switching device (not shown) must be provided on the first carrier 11 so as to enable positioning of the second ends 9 of one of the optical fibers 8 of the first type, coupled to the selected laser diode, relative to the second or the third circle on the second carrier 11. It has been found in practice that a switching time of, for example 20 ms between two successive optical fibers 15 of the second type can be achieved by means of the selection unit 7 shown in FIG. 2.

The holder 17 is provided with exit openings 19 for the measurement of the light transported through the part of the breast. The exit openings 19 are coupled to the photodetector unit 21 via further optical conductors 24, for example optical fibers of the second type. The photodetector unit includes, for example 256 photodiodes. The photodiodes are, for example of the Siemens type BPX 63.

During operation of the measuring device, the light generated by the laser diode 2 is applied, via the selected entrance opening 18, into the part of the breast accommodated in the holder. A part of the light transported through the part of the breast is conducted to the photodetector 21 via the exit openings 19. Under the control of an electronic selection unit (not shown), the light intensity on each of the photodiodes in the photodetector unit 21 is successively measured by means of a conventional measuring device. These measurements are repeated while the laser diode 2 is successively optically coupled to each entrance opening 18 of the holder. The measured intensities are stored in the control unit 22. Subsequently, an image is reconstructed from the intensities measured. An example of such a reconstruction is described in U.S. application Ser. No. 08/980756. A possibly present tumor can be localized on the basis of the reconstructed image of the part of the breast.

It has been found that the reconstruction of the image of the part of the breast in the holder is susceptible to variations in the transmission of the optical path between the laser diode and the selected entrance opening in the holder when one and the same entrance opening is selected for successive measurements, for example for the execution of reference measurements. In order to counteract the variations in the transmission in the optical path between the selected laser diode 2 and the selected entrance opening 18, the numerical aperture of each end 12 of the optical fibers 15 of the second type, attached to the second carrier 11 of the selection unit 7, is larger than the numerical aperture of each of the second ends 9 of the optical fibers 8 of the first type which are attached to the first carrier 10. Furthermore, the diameter of the optical fiber 15 of the second type is preferably larger than the diameter of the optical fiber 8 of the first type. An example of an optical fiber of the first type is, for example a multimode quartz optical fiber having an aperture of 0.39 and a diameter of 400 µm, for example the type FT-400-UMT as marketed by the company 3M. An example of an optical fiber of the second type is a multimode quartz optical fiber having an aperture of 0.48 and a diameter of 1000 µm, for example the type FT-1.0-URT as marketed by the company 3M.

Figure 2:
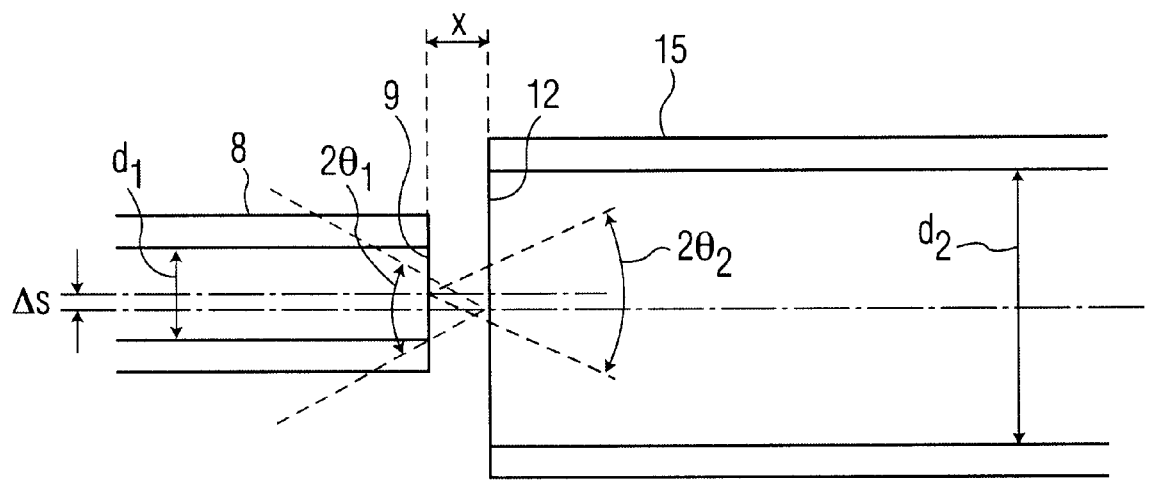
FIG. 2 shows a second end of a first optical fiber which is coaxially arranged relative to a second end of a second optical fiber.
Figure 3:
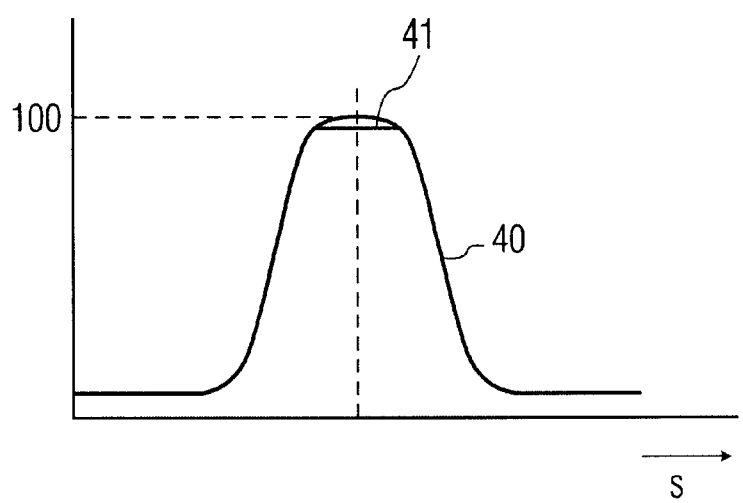
FIG. 3 shows a transmission characteristic of a selection unit.

FIG. 2 shows an example of an optical fiber 8 of the first type which is coaxially arranged relative to an optical fiber 15 of the second type. The diameter d1 of the optical fiber 8 of the first type amounts to 400 µm and its numerical aperture is 0.39; the diameter d2 of the optical fiber 15 of the second type is 1000 µm and its numerical aperture is 0.48. The angle of aperture $2\theta_2$ of the first end of the optical fiber of the second type, therefore, is larger than the angle of aperture $2\theta_1$ of the second end 9 of the optical fiber of the first type. The distance x between the second end 9 of the optical fiber of the first type and the first end 12 of the optical fiber of the second type amounts to, for example 200 µm. The tolerance Δs in respect of the coaxial position of the second end 9 of the optical fiber of the first type relative to the first end 12 of the optical fiber of the second type may amount to 150 µm at the most; the variation in the transmission between the laser diode 2 and the selected entrance opening 18 then remains less than 0.1%. FIG. 3 shows a transmission characteristic 40 as a function of the coaxial shift s of the second end 9 of the optical fiber 8 of the first type and the first end 12 of an optical fiber 15 of the second type. Because of the larger aperture of the first end 12 of the optical fiber relative to the aperture of the second end 9 of the optical fiber of the first type, the optical transmission of the selection unit 7 is less susceptible to positioning errors Δs regarding the coaxial position of the ends 9, 12 of the optical fiber 8 of the first type and the optical fiber 15 of the second type; this is represented by the horizontal part 41 of the transmission characteristic in FIG. 3. Furthermore, when the described selection unit is used, the crosstalk between neighboring optical fibers will be less than −90 dB.

In order to enable compact assembly of the optical fibers with the holder 17 for the optical medium in the device 1, the exit optical conductor 15 preferably also includes optical fibers 16 of a third type, for example, a multimode synthetic fiber having a diameter of 1 mm and a numerical aperture of 0.48, for example the Hewlett Packard type HFBR-QMS. An advantage of such a multimode synthetic optical fiber consists in that the minimum radius of curvature of a bend in a multimode synthetic fiber can be much smaller than the minimum radius of curvature of a bend that can be achieved in the case of a multimode quartz fiber. For example, the minimum radius of curvature for the multimode synthetic fiber is 35 mm whereas that for the multimode quartz fiber is, for example 67 mm.

Figure 4:
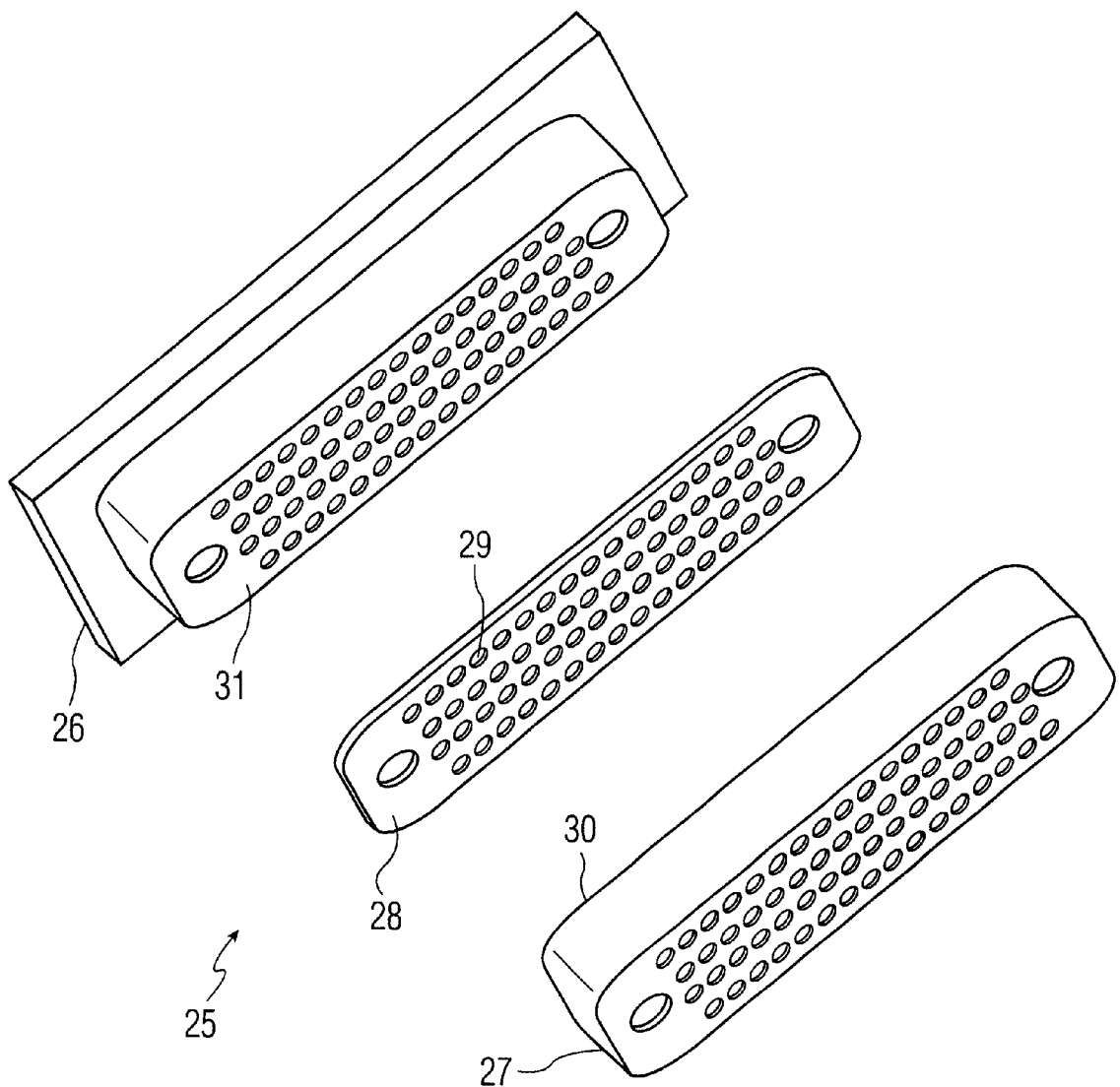
FIG. 4 shows an optical connector unit.

In order to improve the transmission of the optical path between the laser diode and the selected entrance opening, the multimode synthetic fiber 16 is replaced by the multimode quartz fiber 15 at some distance (for example, 30 cm) from the holder 17. The reason for doing so is that the damping of the multimode quartz fiber is lower than that of the multimode synthetic fiber. In order to couple the fibers of the second type 15 and the fibers of the third type 16 to one another, the device includes an optical fiber connector unit 25 which is inserted in the exit light conductor 15. FIG. 4 shows such an optical fiber connector unit 25. FIG. 4 shows an optical connector unit 25 which includes a first section 26 and a second section 27, the first section 26 being arranged to receive the second ends of the optical fibers of the second type whereas the second section 27 is arranged to receive a first end of optical fibers of a third type.

In order to counteract crosstalk between the ends of the optical fibers of the third type, the optical connector unit also contains a light-absorbing material 28 which is arranged between the first section 26 and the second section 27 upon assembly of the connector unit, the light-absorbing material 28 being provided with light-conducting channels 29 for optically coupling the optical fibers of the second type to the optical fibers of the third type. The length of such a light-conducting channel 29 amounts to, for example 0.5 mm and its diameter is, for example 2 mm. Use is preferably made of a light-absorbing material having elastic properties, so that the tolerances in the areas 30, 31 which adjoin one another upon assembly may be greater and hence the manufacture of the sections is simpler. Rubber is an example of such a light-absorbing elastic material. Black paper is another example in this respect.

The light conductors between the exit openings 19 and the photodetector unit 21 in the device 21 may also include optical fibers of the third type so as to enable compact assembly of the optical fibers with the holder; an optical connector unit which is identical to the optical connector unit 25 then serves to couple the optical fibers of the third type, being coupled to the exit openings 19 of the holder, to optical fibers of the second type which are coupled to the photodetector unit 21.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A device for localizing an object in a turbid medium, comprising a light source; a photodetector unit; a holder for accommodating the turbid medium, which holder is constructed to include: (1) a plurality of entrance openings for coupling light generated by the light source into the turbid medium, and (2) a plurality of exit openings, constructed to communicate light present at one of the exit openings to the photodetector unit; a selection unit for optically coupling the light source to an entrance opening to be selected from the plurality of entrance openings; wherein the selection unit includes means for counteracting variations in a transmission within an optical path formed between the light source and the selected entrance opening.

2. A device as claimed in claim 1, wherein the means for counteracting variations comprises an entrance light conductor and an exit light conductor, a first end of said entrance light conductor being optically coupled to the light source whereas a second end is positioned so as to be displaceable for the optical coupling to a first end of one of the exit light conductors, a second end of said exit light conductor being coupled to the selected entrance opening; and wherein a numerical aperture of the first end of each exit light conductor is larger than a numerical aperture of the second end of the entrance light conductor.

3. A device as claimed in claim 2, wherein the entrance light conductor of the selection unit includes an optical fiber of a first type and that each exit light conductor of the selection unit includes an optical fiber of a second type.

4. A device as claimed in claim 3, wherein each exit light conductor also includes an optical fiber of a third type which has a property deviating from that of the optical fiber of the second type and is optically coupled, via a fiber-optical connector unit, to the optical fiber of the second type of the same exit light conductor.

5. A device as claimed in claim 4, wherein the optical fiber of the second type contains quartz.

6. A device as claimed in claim 4 wherein the optical fiber of the third type contains a synthetic material.

7. A device as claimed in claim 4, wherein the fiber-optical connector unit includes a first section which contains a second end of the optical fiber of the second type; a second section which contains a first end of the optical fiber of the third type; and a light-absorbing material arranged between the first section and the second section and provided with a light-conducting channel for optically coupling the optical fiber of the second type to the optical fiber of the third type.

8. A device as claimed in claim 7, wherein the light-absorbing material also has elastic properties.

* * * * *